United States Patent
Boyd et al.

(10) Patent No.: US 9,488,628 B2
(45) Date of Patent: Nov. 8, 2016

(54) GAS SENSOR PROTECTION DEVICE AND METHOD

(71) Applicant: Robert Bosch GmbH, Stuttgart (DE)

(72) Inventors: David Boyd, Greenville, SC (US); Craig Magera, Simpsonville, SC (US)

(73) Assignee: Robert Bosch GmbH, Stuttgart (DE)

( * ) Notice: Subject to any disclaimer, the term of this patent is extended or adjusted under 35 U.S.C. 154(b) by 168 days.

(21) Appl. No.: 14/155,909

(22) Filed: Jan. 15, 2014

(65) Prior Publication Data
US 2015/0075253 A1    Mar. 19, 2015

Related U.S. Application Data

(60) Provisional application No. 61/879,403, filed on Sep. 18, 2013.

(51) Int. Cl.
*G01N 27/407* (2006.01)
*G01N 33/00* (2006.01)
*G01M 15/10* (2006.01)

(52) U.S. Cl.
CPC ........ *G01N 33/0036* (2013.01); *G01M 15/104* (2013.01); *G01N 27/4077* (2013.01)

(58) Field of Classification Search
CPC .................................................. G01N 27/4077
See application file for complete search history.

(56) References Cited

U.S. PATENT DOCUMENTS

| | | | |
|---|---|---|---|
| 5,445,548 A * | 8/1995 | Koishikawa | G01N 1/2252 123/703 |
| 6,348,141 B1 | 2/2002 | Kato et al. | |
| 7,360,414 B2 | 4/2008 | Konzelmann et al. | |
| 8,449,743 B2 | 5/2013 | Sekiya et al. | |
| 8,464,573 B2 | 6/2013 | Sekiya et al. | |
| 2004/0144645 A1 | 7/2004 | Yamada et al. | |
| 2007/0251823 A1 | 11/2007 | Yamada | |
| 2008/0028831 A1 | 2/2008 | Nakashima et al. | |
| 2008/0067066 A1 | 3/2008 | Okumura et al. | |
| 2008/0105037 A1 | 5/2008 | Nakashima et al. | |

FOREIGN PATENT DOCUMENTS

DE    102012017076 A1    3/2013

OTHER PUBLICATIONS

European Search Report for EP Appl. 14180911.1 dated Feb. 5, 2015, 6 pages.

* cited by examiner

*Primary Examiner* — Michael A Lyons
*Assistant Examiner* — Alex Devito
(74) *Attorney, Agent, or Firm* — Michael Best & Friedrich LLP

(57) ABSTRACT

A gas sensor includes a sensor housing and a sensing element located within the sensor housing. The sensing element has a distal end and defines an axis. The gas sensor also includes a sensor protection device coupled to the sensor housing and at least partially surrounding the distal end of the sensing element. The sensor protection device includes a first member coupled to the housing, the first member having a generally rectangular cross-sectional shape in a plane perpendicular to the axis. The first member includes a gas inlet and a gas outlet. The sensor protection device also includes a second member coupled to the housing.

15 Claims, 6 Drawing Sheets

GAS SENSOR PROTECTION DEVICE AND METHOD

CROSS REFERENCE TO RELATED APPLICATIONS

This application claims priority to U.S. Provisional Application No. 61/879,403, filed Sep. 18, 2013, the entire contents of which are incorporated herein by reference.

STATEMENT REGARDING FEDERALLY SPONSORED RESEARCH OR DEVELOPMENT

This invention was made with Government support under DE-EE0005975 awarded by the Department of Energy. The Government has certain rights in this invention.

BACKGROUND

The present invention relates to a gas sensor, in particular a gas sensor having a sensor protection device for use in internal combustion engines.

Oxygen gas sensors are normally located after the combustion process in the exhaust flow of an internal combustion engine. In this location, the oxygen gas sensor is exposed mostly to hot exhaust gases. Oxygen gas sensors located before the combustion process, for example in the intake manifold, are exposed to cooler air that may have contaminants such as water, oil, fuel vapor, soot, particles, and other contaminants. These contaminants can cause damage to the oxygen gas sensor including thermal shock cracks, poisoning of the sensor element, and clogging of passage ways, among other things.

SUMMARY

In accordance with one construction, a gas sensor includes a sensor housing and a sensing element located within the sensor housing. The sensing element has a distal end and defines an axis. The gas sensor also includes a sensor protection device coupled to the sensor housing and at least partially surrounding the distal end of the sensing element. The sensor protection device includes a first member coupled to the housing, the first member having a generally rectangular cross-sectional shape in a plane perpendicular to the axis. The first member includes a gas inlet and a gas outlet. The sensor protection device also includes a second member coupled to the housing.

In accordance with another construction, a gas sensor includes a sensor housing and a sensing element disposed within the sensor housing. The sensing element has a distal end and defines an axis. The gas sensor also includes a sensor protection device coupled to the sensor housing and at least partially surrounding the distal end of the sensing element. The sensor protection device includes a first member coupled to the housing, the first member having a generally rectangular cross-sectional shape in a plane perpendicular to the axis. The first member includes a first sidewall having a gas inlet and a second, opposite sidewall having a gas outlet. The first member at least partly defines an open channel extending between the gas inlet and the gas outlet, the open channel having a first cross-sectional area, a second cross-sectional area, and a third cross-sectional area between the gas inlet and the gas outlet, the third cross-sectional area being smaller than both the first and second cross-sectional areas such that gas passing through the open channel experiences lower pressure and higher velocity in the third cross-sectional area as compared with both the first and second cross-sectional areas. The sensor protection device also includes a second member coupled to the housing, the second member having a first sidewall directly coupled to the first sidewall of the first member, a second, opposite sidewall having a gas inlet, and an end wall disposed between the first and second sidewalls of the second member, the end wall having a gas outlet.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 7:
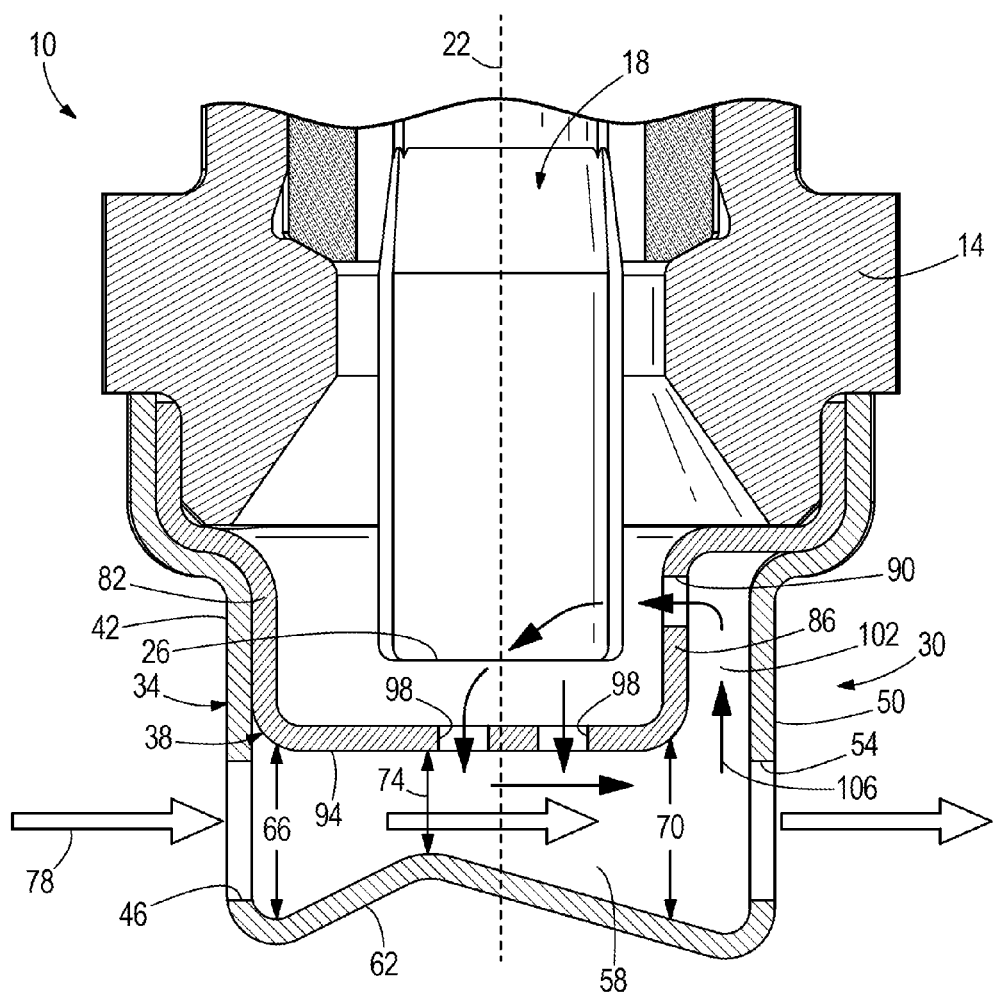
FIG. 7 is a partial cross-sectional view of the gas sensor of FIG. 1, as taken along lines 7-7 in FIG. 1.
Figure 8:
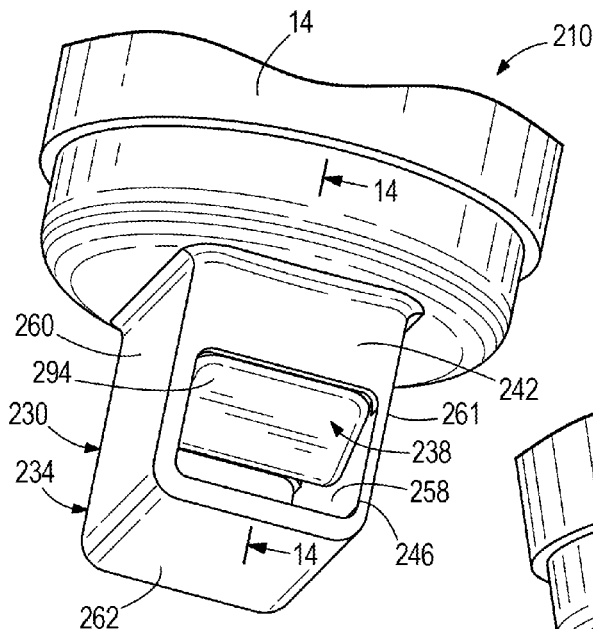
FIGS. 8 and 9 are partial perspective views of a gas sensor according to another construction of the invention, the gas sensor including a sensor protection device.
Figure 9:
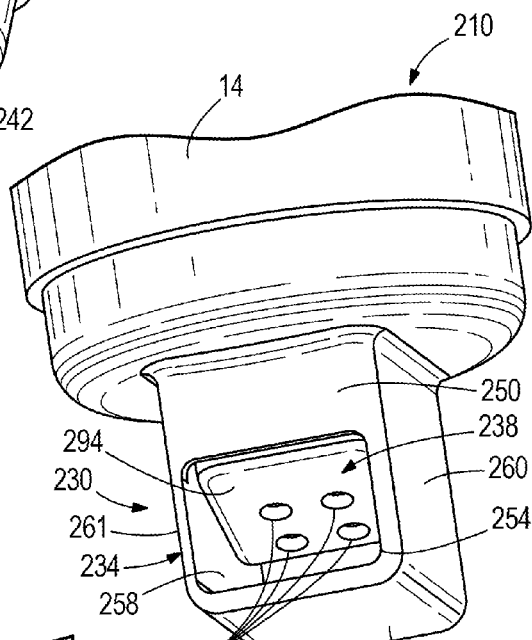
Figure 10:
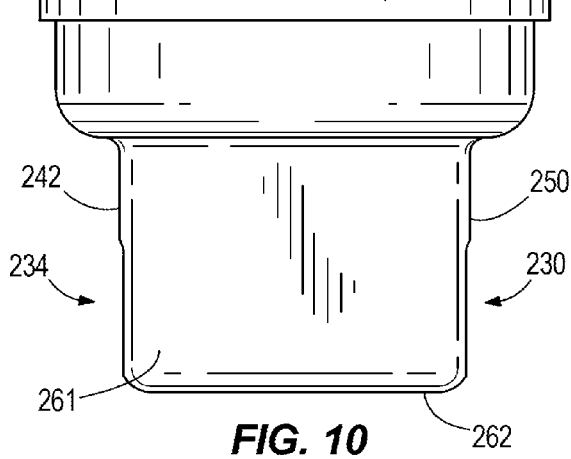
FIG. 10 is a partial side view of the gas sensor of FIG. 8.
Figure 11:
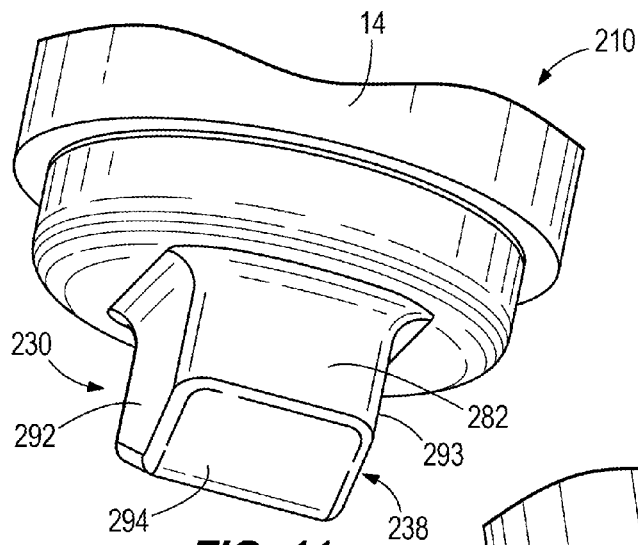
FIGS. 11 and 12 are partial perspective views of the gas sensor of FIG. 8, with an outer member of the sensor protection device removed.
Figure 12:
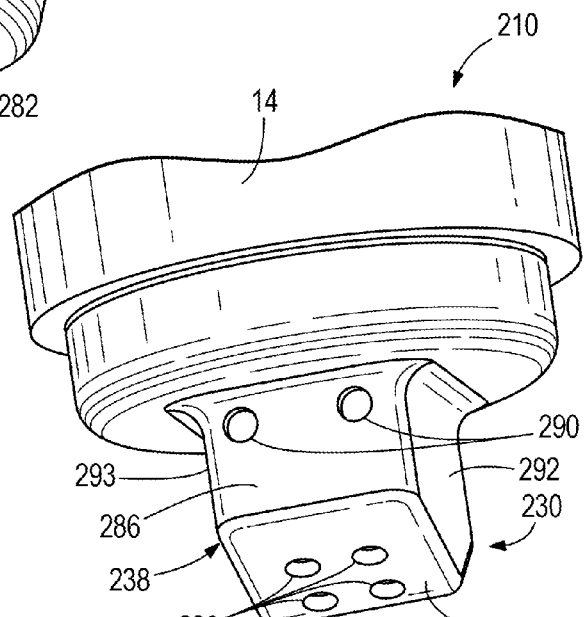
Figure 13:
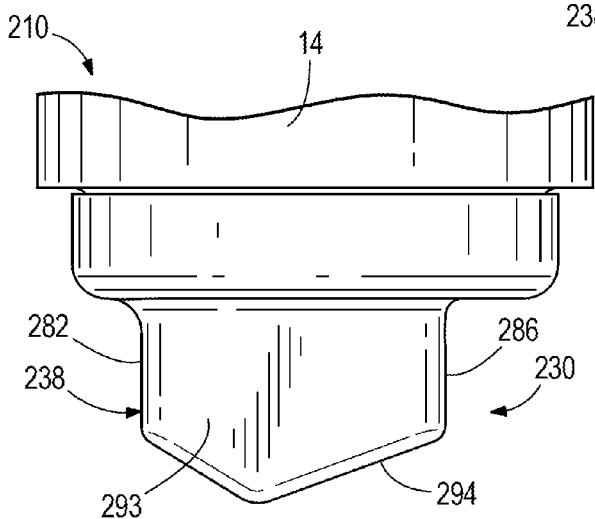
FIG. 13 is a partial side view of the gas sensor of FIG. 8, with the outer member of the sensor protection device removed.

FIGS. 1-7 illustrate a gas sensor 10. The gas sensor 10 includes a sensor housing 14 and a sensing element 18 (FIG. 7) disposed within the sensor housing 14. The sensing element 18 is an oxygen sensor, although other types of sensing elements 18 are also possible. As illustrated in FIG. 7, the sensing element 18 defines an axis 22, and includes a distal end 26.

The gas sensor 10 further includes a sensor protection device 30. The protection device 30 is coupled to the housing 14 and at least partially surrounds the distal end 26 of the sensing element 18. The protection device 30 includes a first, outer member 34 and a second, inner member 38. The inner member 38 is disposed within the outer member 34, and the distal end 26 of the sensing element is disposed within the inner member 38. The inner member 38 is coupled to the housing 14, and the outer member 34 is coupled to both the housing 14 and to the inner member 38. In some constructions one or more of the outer member 34 and the inner member 38 are integrally formed with the housing 14 and/or with each other. In some constructions one or more of the outer member 34 and the inner member 38 are removably coupled with the housing 14.

The outer member 34 has a generally rectangular cross-sectional shape in a plane perpendicular to the axis 22. As will be discussed further below, this generally rectangular cross-sectional shape facilitates the desired gas flow through the protection device 30. The outer member 34 includes a first sidewall 42 having a generally rectangular gas inlet 46, a second, opposite sidewall 50 having a generally rectangular gas outlet 54, and an open channel 58 extending generally perpendicular to the axis 22 between the gas inlet 46 and the gas outlet 54. The gas inlet 46 and the gas outlet 54 are approximately 180 degrees apart from one another on the gas sensor 10. The outer member 34 also includes two sidewalls 60, 61 that are generally perpendicular to the sidewalls 42, 50, and that do not include any gas inlets or gas outlets. The sidewalls 42, 50 are generally parallel to one another, and the sidewalls 60, 61 are generally parallel to one another. Other constructions include different shapes for the gas inlet 46 and the gas outlet 54. In some constructions more than one gas inlet 46 and/or gas outlet 54 are provided.

As illustrated in FIG. 7, the open channel 58 is formed in part by an end wall 62 of the outer member 34. The end wall 62 extends between the sidewalls 42, 50, and has an angled, non-linear profile that forms converging and diverging cross-sections within the channel 58. For example, and with continued reference to FIG. 7, the channel 58 has a first cross-sectional area 66 taken along a plane parallel to the axis 22, a second cross-sectional area 70 taken along a plane parallel to the axis 22, and a third cross-sectional area 74 taken along a plane parallel to the axis 22. The third cross-sectional area 74 is disposed between the first and second cross-sectional areas 66, 70, and is smaller than both the first and second cross-sectional areas 62, 66. The third cross-sectional area 74 is the smallest cross-sectional area through which gas moves in the channel 58. The third cross-sectional area 74 is disposed generally in a middle portion of the channel 58. Other constructions include different sizes and shapes of cross-sectional areas than those illustrated.

With continued reference to FIG. 7, a main flow of gas 78 (including a contaminant mass found therein) enters the protection device 30 through the gas inlet 46 and is manipulated by Bernoulli's Principle of flow within the channel 58, such that the gas flow 78 passing through the outer member 34 experiences lower pressure and higher velocity in the third cross-sectional area 74 as compared with both the first and second cross-sectional areas 66, 70. The outer member 34 converges in cross-sectional area from the first cross-sectional area 66 to the third cross-sectional area 74, and diverges in cross-sectional area from the third cross-sectional area 74 to the second cross-sectional area 70. At the third cross-sectional area 74 the velocity of the gas flow 78 increases with a simultaneous decrease in pressure. As the gas flow 78 moves from the third cross-sectional area 74 toward the gas outlet 54, the velocity of the gas flow 78 decreases and the pressure increases. The majority of the gas flow 78 between the gas inlet 46 and the gas outlet 54 passes through the protection device 30 in a direction perpendicular to the axis 22 without influencing the sensing element 18. Because of the generally rectangular cross-sectional structure of the outer member 34 and the locations of the gas inlet 46 and the gas outlet 54, the gas flow 78 is a generally linear gas flow through the protection device 30.

With reference to FIGS. 1-7, the inner member 38 has a generally rectangular cross-sectional shape in a plane perpendicular to the axis 22. As will be discussed further below, this generally rectangular cross-sectional shape also facilitates the desired gas flow through the protection device 30.

Figure 1:
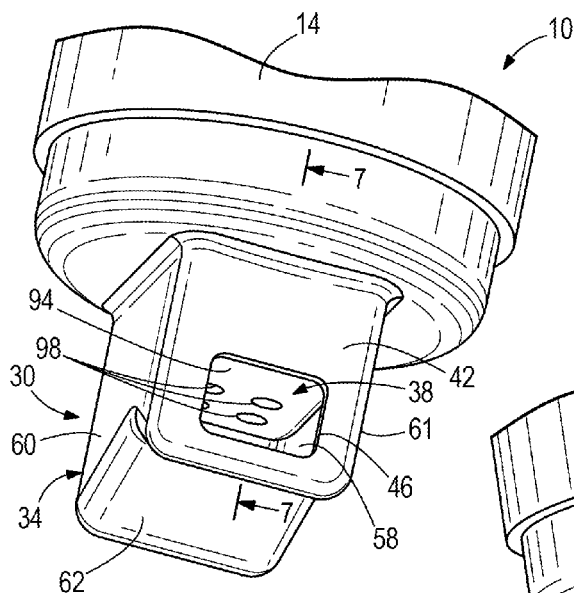
FIGS. 1 and 2 are partial perspective views of a gas sensor according to one construction of the invention, the gas sensor including a sensor protection device.
Figure 2:
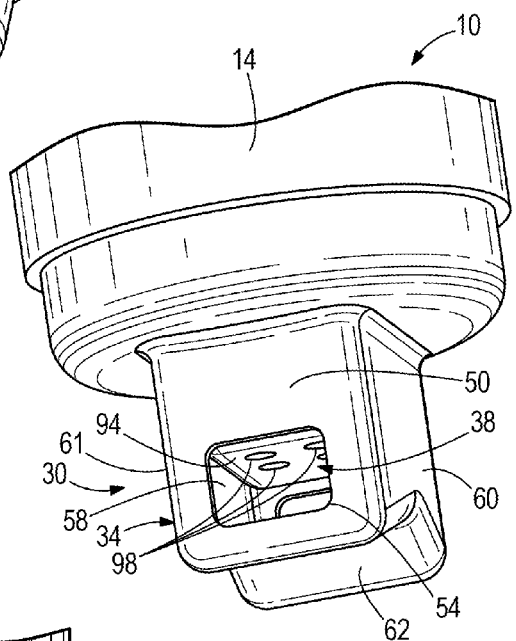
Figure 3:
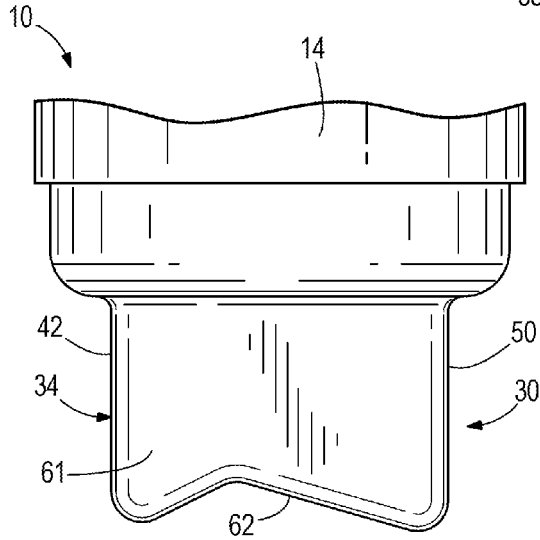
FIG. 3 is a partial side view of the gas sensor of FIG. 1.
Figure 4:
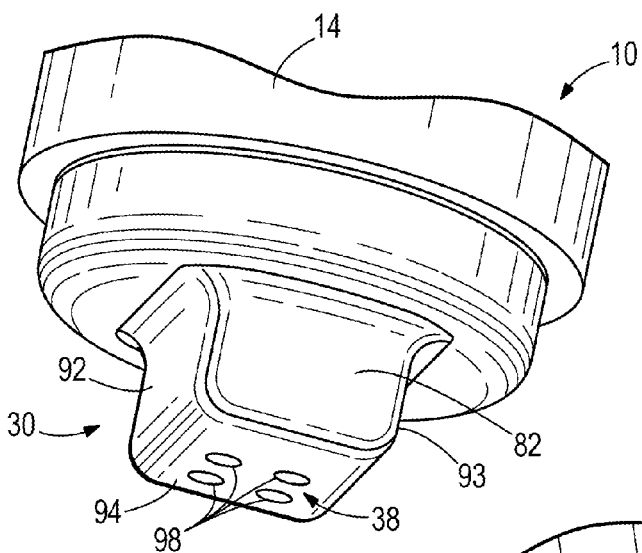
FIGS. 4 and 5 are partial perspective views of the gas sensor of FIG. 1, with an outer member of the sensor protection device removed.
Figure 5:
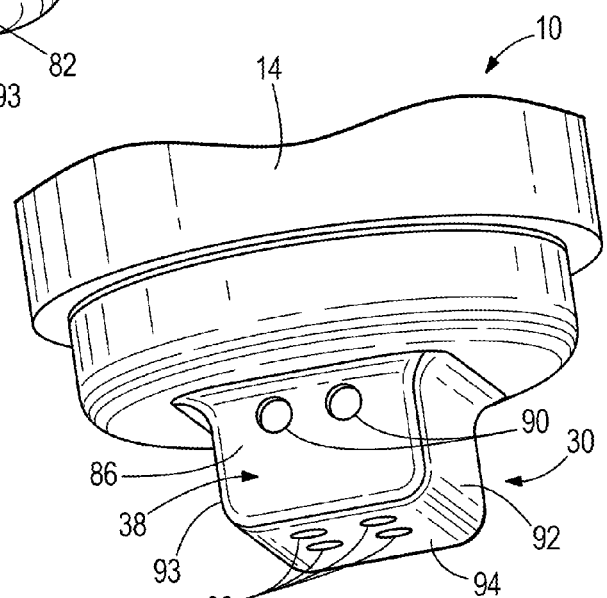
Figure 6:
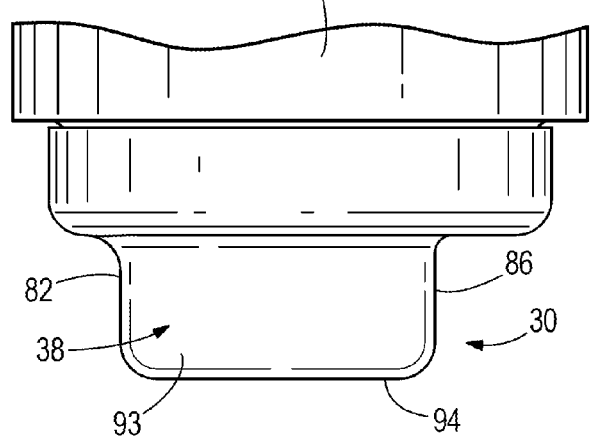
FIG. 6 is a partial side view of the gas sensor of FIG. 1, with the outer member of the sensor protection device removed.

The inner member 38 includes a first sidewall 82 that is coupled directly to the sidewall 42 of the outer member 34 adjacent the gas inlet 46, and does not include any gas inlets or gas outlets. The inner member 38 further includes a second, opposite sidewall 86 that includes a plurality of gas inlets 90 (FIGS. 5 and 7). The inner member also includes two sidewalls 92, 93 that are generally perpendicular to the sidewalls 82, 86, and that do not include any gas inlets or gas outlets. The sidewalls 82, 86 are generally parallel to one another, and the sidewalls 93, 93 are generally parallel to one another. The inner member 38 further includes an end wall 94 disposed between the sidewalls 82, 86. The end wall 94 includes a plurality of gas outlets 98. As illustrated in FIG. 7, the gas outlets 98 are disposed between the third cross-sectional area 74 and the gas outlet 54, generally in a middle portion of the open channel 58 and downstream of the third cross-sectional area 74. Other constructions include different numbers, shapes, patterns, and locations of gas inlets 90 and gas outlet 94 other than that illustrated.

With reference to FIG. 7, the protection device 30 also includes a chamber 102 formed between the sidewall 86 and the sidewall 50. The chamber 102 extends generally parallel to the axis 22, and is in direct fluid communication with both the channel 58 and the gas inlets 90.

With reference to FIG. 7, because of the higher pressure of the gas flow 78 at the gas outlet 54 as compared to the third cross-sectional area 74, a portion 106 of the gas flow 78 (as illustrated by the smaller, circulating arrows in FIG. 7) is induced (e.g., drawn up) into the chamber 102 toward the gas inlets 90. This portion 106 circulates through the gas inlets 90 in a direction generally perpendicular to the axis 22, over the distal end 26 of the sensing element 18, and then out through the gas outlets 98 in a direction generally parallel to the axis 22 and back into the channel 58, rejoining the main gas flow 78. As illustrated in FIG. 7, the circulating portion 106 creates a sampling of gas across the sensing element 18. The momentum of the contaminant mass in the main gas flow 78 keeps the contaminant mass moving within channel 58 in a direction generally perpendicular to the axis 22, such that all (or at least a substantial portion) of the contaminant mass in the main gas flow 78 does not move into the circulating portion 106 and does not enter the gas inlets 90, thereby protecting the sensing element 18 from damage or contamination from the contaminant mass in the main gas flow 78.

FIGS. 8-14 illustrate a gas sensor 210 having an outer member 234 with an end wall 262 and an inner member 238 with an end wall 294. The gas sensor 210 is identical to the gas sensor 10, with the exception of the geometry of the end walls 262 and 294. Like parts have been given like reference numbers, while similar parts have been given reference numbers that are increased by 200.

Figure 14:
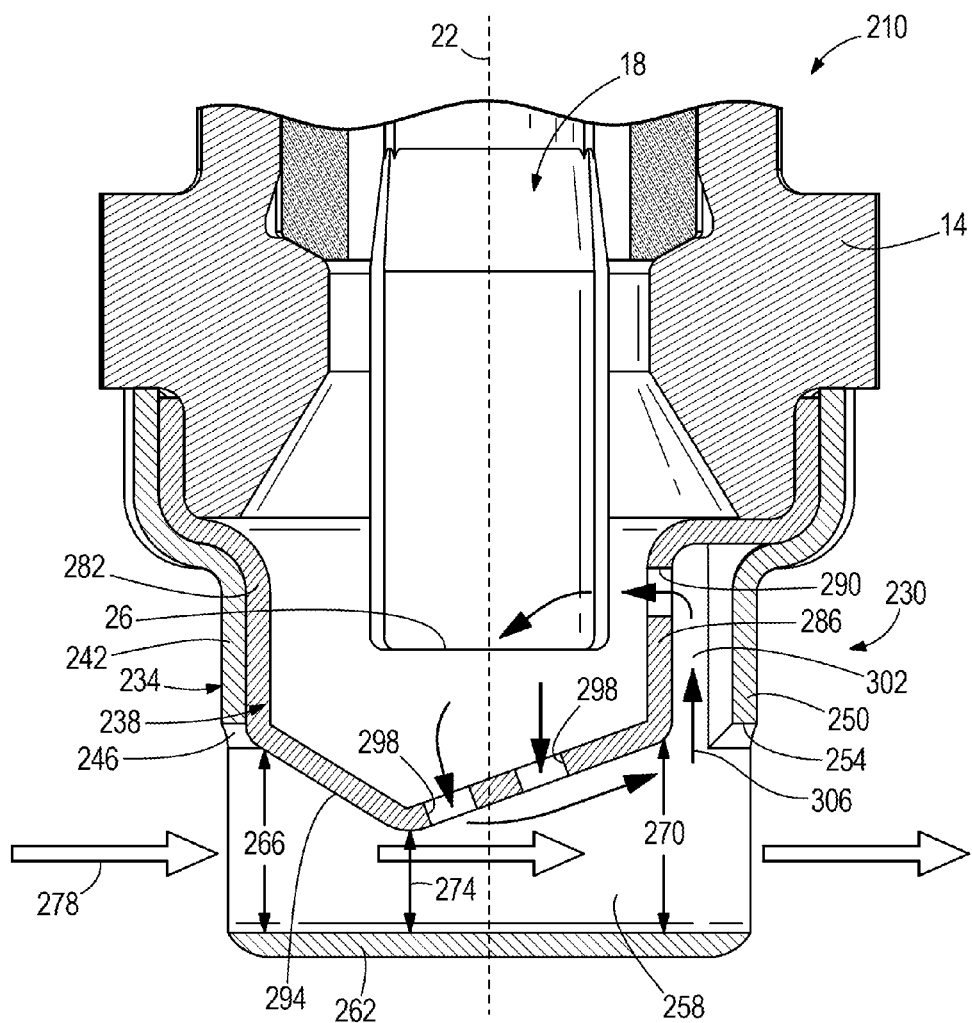
FIG. 14 is a partial cross-sectional view of the gas sensor of FIG. 8, as taken along lines 14-14 in FIG. 8.

As illustrated in FIG. 14, the end wall 262 is generally flat or planar, and the end wall 294 includes a non-linear profile, in contrast to FIG. 7 where the end wall 94 is generally flat or planar, and the end wall 62 has the non-linear profile. Thus, in the construction illustrated in FIGS. 8-14, the converging and diverging cross-sectional areas of the protection device 230 are formed by the non-linear profile of the end wall 294 on the inner member 238. In the construction illustrated in FIGS. 1-7, the converging and diverging cross-sectional areas of the protection device 30 are formed by the non-linear profile of the end wall 62 on the outer member 34.

In other constructions the converging and diverging cross-sectional areas of the protection devices are formed with both the inner and outer protection devices having non-linear profiles (e.g., with both end walls having non-linear profiles). In some constructions the converging and diverging cross-sectional areas are formed by having a non-linear profile in a different plane around a direction of the gas flow 78 other than that illustrated in FIGS. 1-14 (e.g., a construction with one or more sidewalls of the outer and inner members having a non-linear profile as opposed to one or more end walls of the outer and inner members having a non-linear profile).

With continued reference to FIG. 14, the protection device 230 includes an open channel 258 with a first cross-sectional area 266 taken along a plane parallel to the axis 22, a second cross-sectional area 270 taken along a plane parallel to the axis 22, and a third cross-sectional area 274 taken along a plane parallel to the axis 22. The inner member 238 includes gas outlets 298 that are disposed downstream of the third cross-sectional area 274 and are protected, at least in part, by the non-linear shape of the end wall 294 from a direct gas flow 278 that initially enters the outer member 234

Various features and advantages of the invention are set forth in the following claims.

What is claimed is:

1. A gas sensor comprising:
    a sensor housing;
    a sensing element located within the sensor housing, the sensing element having a distal end and defining an axis; and
    a sensor protection device coupled to the sensor housing and at least partially surrounding the distal end of the sensing element, the sensor protection device including
        a first member coupled to the housing, the first member having a generally rectangular cross-sectional shape in a plane perpendicular to the axis, the first member including a gas inlet and a gas outlet; and
        a second member coupled to the housing;
    wherein the axis extends through each of the distal end of the sensing element, the first member, and the second member, and passes between the gas inlet and the gas outlet;
    wherein the first member includes a first sidewall including the gas inlet, a second, opposite sidewall including the gas outlet, and an end wall disposed between the first and second sidewalls;
    wherein the second member includes a first sidewall, a second, opposite sidewall, and an end wall disposed between the first and second sidewalls of the second member;
    wherein the end wall of at least one of the first and second members includes a ramped profile, wherein moving along the ramped profile from the first sidewall toward the second sidewall of the at least one of the first and second members, the ramped profile rises and falls relative to a direction perpendicular to the axis, wherein the ramped profile includes first and second planar portions that form a general V-shape in cross-section, such that an open channel having a converging and diverging cross-section is formed within the sensor protection device by the ramped profile.

2. The gas sensor of claim 1, wherein the first member is an outer member, and the second member is an inner member disposed within the outer member.

3. The gas sensor of claim 1, wherein the gas inlet has a generally rectangular shape and the gas outlet has a generally rectangular shape.

4. The gas sensor of claim 1, wherein the gas inlet and the gas outlet are positioned to direct a flow of gas in a direction generally perpendicular to the axis.

5. The gas sensor of claim 1, wherein the open channel has a first cross-sectional area, a second cross-sectional area, and a third cross-sectional area between the gas inlet and the gas outlet, the third cross-sectional area being smaller than both the first and second cross-sectional areas such that gas passing through the open channel experiences lower pressure and higher velocity in the third cross-sectional area as compared with both the first and second cross-sectional areas.

6. The gas sensor of claim 5, wherein the second member includes a gas inlet and a gas outlet, the gas outlet of the second member in direct fluid communication with the open channel.

7. The gas sensor of claim 6, wherein the gas outlet of the second member is positioned so as to direct a flow of gas in a direction generally parallel to the axis.

8. The gas sensor of claim 6, wherein the gas inlet of the second member is positioned so as to direct a flow of gas in a direction generally perpendicular to the axis.

9. The gas sensor of claim 6, wherein the sensor protection device includes a chamber disposed adjacent the open channel, the chamber disposed between the first and second members, and wherein the gas inlet of the second member is in direct communication with the chamber.

10. The gas sensor of claim 6, wherein the gas inlet of the second member is disposed on the second sidewall of the second member, and the gas outlet of the second member is disposed on the end wall of the second member.

11. The gas sensor of claim 2, wherein the end wall of the first member includes the ramped profile.

12. The gas sensor of claim 1, wherein the first sidewall of the second member is coupled directly to the first sidewall of the first member.

13. The gas sensor of claim 2, wherein the end wall of the second member includes the ramped profile.

14. The gas sensor of claim 1, wherein a portion of a gas flow moving through the open channel is drawn away from the open channel and through a gas inlet and gas outlet of the second member.

15. The gas sensor of claim 13, wherein a gas outlet is disposed on the ramped profile of the end wall of the second member.

\* \* \* \* \*